United States Patent [19]

Smith

[11] 4,005,112
[45] Jan. 25, 1977

[54] MULTISTEP METHOD FOR PREPARATION OF TETRAHYDROFURAN STARTING FROM PROPYLENE, OXYGEN AND A CARBOXYLIC ACID

[75] Inventor: William E. Smith, Schenectady, N.Y.

[73] Assignee: General Electric Company, Pittsfield, Mass.

[22] Filed: May 27, 1975

[21] Appl. No.: 581,265

Related U.S. Application Data

[62] Division of Ser. No. 420,581, Dec. 3, 1973, abandoned.

[52] U.S. Cl. .................................. 260/346.1 R
[51] Int. Cl.$^2$ ............................... C07D 307/08
[58] Field of Search ........... 260/346.1 R, 491, 468

[56] References Cited

UNITED STATES PATENTS

| 3,007,973 | 11/1961 | Weisemann | 260/638 HF |
|---|---|---|---|
| 3,014,970 | 12/1961 | Johnson et al. | 260/638 HF |
| 3,022,340 | 2/1962 | Bloch | 260/491 |
| 3,119,876 | 1/1964 | Jaros et al. | 260/638 HF |
| 3,231,621 | 1/1966 | Slaugh | 260/491 |
| 3,239,566 | 3/1966 | Slaugh et al. | 260/491 |
| 3,239,569 | 3/1966 | Slaugh et al. | 260/491 |
| 3,378,590 | 4/1968 | Usami | 260/632 HF |
| 3,420,898 | 1/1969 | Winkle et al. | 260/491 |
| 3,546,278 | 12/1970 | Heyden et al. | 260/497 A |
| 3,578,698 | 5/1971 | Heyden | 260/491 |
| 3,670,014 | 6/1972 | Fernholz | 260/497 A |

FOREIGN PATENTS OR APPLICATIONS

| 1,170,222 | 11/1969 | United Kingdom | 260/346.1 |
|---|---|---|---|
| 3,670,014 | 6/1972 | United States Of America | 260/497 A |

OTHER PUBLICATIONS

Adkins, J. Am. Chem. Soc., vol. 71, pp. 3051–3055 (49).
Hatch, Higher Oxo Alcohols, pp. 2, 3, 13, 20–23 (1959).

Primary Examiner—Natalie Trousof
Assistant Examiner—Bernard Dentz
Attorney, Agent, or Firm—Donald M. Papuga; William F. Mufatti

[57] ABSTRACT

A process for preparing tetrahydrofuran which comprises heating a carboxylic acid monoester of 1,4-butanediol in the presence of a dehydroacyloxylation catalyst.

2 Claims, No Drawings

000
MULTISTEP METHOD FOR PREPARATION OF TETRAHYDROFURAN STARTING FROM PROPYLENE, OXYGEN AND A CARBOXYLIC ACID

This is a division of application Ser. No. 420,581, filed Dec. 3, 1973, and now abandoned.

This invention relates to a process for preparing tetrahydrofuran which comprises heating a carboxylic acid monoester of 1,4-butanediol in the presence of a dehydroacyloxylation catalyst.

BACKGROUND OF THE INVENTION

It is known in the art that tetrahydrofuran may be made by a number of different methods; the more prominent methods are by the catalytic hydrogenation of furan or by the dehydration of 1,4-butanediol.

In practice, the tetrahydrofuran is most often produced by a series of reactions starting with the reaction of formaldehyde and acetylene in the presence of a cuprous acetylide complex to form butynediol. Butynediol is converted on hydrogenation to butanediol. The 1,4-butanediol is converted to tetrahydrofuran as indicated above.

Additionally, tetrahydrofuran is prepared from maleic acid, its esters, maleic anhydride, fumaric acid, its esters, succinic acid, its esters, succinic anhydride, γ-butyrolactone, or mixtures of these compounds, by hydrogenation over a hydrogenation catalyst.

However, these methods involve considerably expensive equipment and the handling of hazardous materials. Also, catalysts in some cases may be expensive, and in other instances may be easily poisoned.

Tetrahydrofuran is a useful solvent for natural and synthetic resins, particularly vinyls. Also, it is used as an intermediate in the manufacture of nylon, 1,4-dichlorobutane and polyurethanes.

DESCRIPTION OF THE INVENTION

It has been discovered that tetrahydrofuran may be inexpensively prepared from a carboxylic acid monoester of 1,4-butanediol by heating it in the presence of a heterogeneous dehydroacyloxylation catalyst. By this method, tetrahydrofuran is produced in essentially quantitative yields. Also, the dehydroacyloxylation catalyst of the instant invention is stationary and permanent and therefore may be continually reused.

Another object of this invention is to produce tetrahydrofuran from inexpensive starting materials, i.e., propylene, carbon monoxide, hydrogen and oxygen, by way of several intermediate steps.

The dehydroacyloxylation catalysts which may be employed in the practice of this invention are those which promote ring closure and evolution of the carboxylic acid. In the case of the acetate ester, the catalyst is a dehydroacetoxylation catalyst. Suitable dehydroacyloxylation catalysts include zeolites, silica, alumina, silica-aluminas, silica-magnesias, acidic clays and the like.

The zeolite dehydroacyloxylation catalysts which may be used in the instant invention include the synthetic and natural zeolites, also known as molecular sieves. These zeolites are well known in the art and are detailed in *Molecular Sieves*, Charles K. Hersh, Reinhold Publishing Company, New York (1961) which is incorporated herein by reference. Preferably, representative natural zeolites which may be employed in the instant invention include those in Table 3-1, on page 21, of the Hersh reference while representative molecular sieves include those in Table 5-1, on page 54, of the Hersh reference. Additional zeolite catalysts are set forth in *Organic Catalysts Over Crystalline Aluminosilicates*, P. B. Venuto and P. S. Landis, Advances in Catalysis, Vol. 18, pp. 259 to 371 (1968), incorporated herein by reference.

The silica-alumina dehydroacyloxylation catalysts which may be used vary in composition from pure silica to pure alumina whereas the silica-magnesias vary in composition from pure silica to predominantly magnesia.

The acidic clay dehydroacyloxylation catalysts which may be used in the instant invention include clays containing the minerals kaolinite, halloysite, montmorillonite, illite, quartz, calcite, liminomite, gypsum, muscavite and the like, either in naturally acidic forms or after treatment with acid.

The catalyst is preferably used in the form of a bed through which the reactants are passed.

The carboxylic acid monoesters of 1,4-butanediol which are suitable in the instant invention preferably contain 2 to 8 carbon atoms. A preferred carboxylic acid monoester of 1,4-butanediol is 4-acetoxybutanol.

The temperature at which the process can be carried out varies widely. Temperatures ranging from about 125° to about 300° C. are generally adequate although higher temperatures can be used. Preferably, the reaction is carried out at a temperature of from about 150° to about 250° C. The maximum depends upon destruction of the product, olefin formation occurring under too rigorous conditions.

Although only atmospheric pressure is normally required, it will be of course apparent to those skilled in the art that superatmospheric pressure or subatmospheric pressure may be used where conditions and concentrations so dictate.

The process may be illustrated, taking 4-acetoxybutanol as an example, by the following equation:

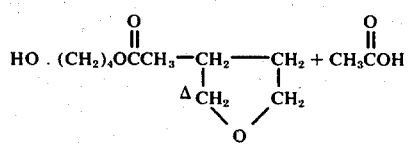

In copending application A, Ser. No. 365,228 of William E. Smith, filed May 30, 1973 and assigned to the same assignee as the present invention and now abandoned, there is disclosed and claimed a process for making butanediols by reacting propylene, oxygen and a carboxylic acid to produce an allyl carboxylate which is then hydroformylated to produce the mixture of the corresponding aldehydes. Hydrogenation of the mixture produces a mixture of the esters of the corresponding diols. In copending application B, Ser. No. 365,231 of William E. Smith, filed May 30, 1973 and assigned to the same assignee as the present invention and now abandoned, there is disclosed and claimed a process wherein the hydrogenation is accomplished concurrently with the hydroformylation reaction. De-esterification of the diol ester mixture produces the desired butanediols which can be separated by distillation. These copending applications A and B are incorporated herein by reference.

In carrying out the preparation of tetrahydrofuran starting from propylene, oxygen and a carboxylic acid, the procedures disclosed in copending applications A and B may be used to obtain the carboxylic acid esters of 1,4-butanediol. These involve (a) reacting propylene, oxygen and a carboxylic acid to form the corresponding allyl carboxylate; (b) converting the allyl carboxylate under hydroformylation-hydrogenation conditions to a mixture comprising the carboxylic acid esters of 1,4-butanediol, 1,2-butanediol and 2-methyl-1,3-propanediol; (c) heating the diol esters in the presence of a dehydroacyloxylation catalyst to form tetrahydrofuran and the carboxylic acid; and (d) isolating the carboxylic acid in a form suitable for recycling to (a).

To varying extents, depending on reaction conditions, the 1,4-butanediol diester is formed in this sequence, either by disproportionation of the monoester (which affords the diester and diol) or by further esterification of the monoester with the carboxylic acid present as a decomposition product.

Specifically, this overall process for preparing tetrahydrofuran comprises (a) reacting propylene, oxygen and a carboxylic acid in the presence of a catalyst comprising a Group VIII noble metal, or its salts, or its oxides or mixtures thereof at a temperature sufficiently high to provide the desired rate of formation of the corresponding allyl carboxylate but below the temperature at which substantial degradation of the allyl carboxylate occurs; (b) converting the allyl carboxylate under hydroformylation-hydrogenation conditions to a mixture comprising the carboxylic acid esters of 1,4-butanediol, 1,2-butanediol and 2-methyl-1,3-propanediol; (c) heating said mixture in the presence of a dehydroacyloxylation catalyst to convert the 1,4-butanediol monoester present, as well as any diol, to tetrahydrofuran and the carboxylic acid; and (d) isolating the carboxylic acid in a form suitable for recycling to (a).

More specifically, the process of producing tetrahydrofuran comprises (a) reacting propylene, oxygen and acetic acid in the presence of a catalyst comprising a Group VIII noble metal, or its salts or its oxides or mixtures thereof at a temperature sufficiently high to provide the desired rate of formation of allyl acetate but below the temperature at which substantial degradation of allyl acetate occurs; (b) converting the allyl acetate under hydrogenation-hydroformylation conditions to a mixture comprising 1,4-butanediol monoacetate, 1,4-butanediol diacetate, 1,4-butanediol and the corresponding derivatives of 2-methyl-1,3-propanediol and 1,2-butanediol; (c) heating said mixture in the presence of a dehydroacetoxylation catalyst to convert the monoacetate of 1,4-butanediol as well as the diol present to tetrahydrofuran and acetic acid; (d) isolating the acetic acid in a form suitable for recycling to (a).

The conditions under which the carboxylic acid esters of 1,4-butanediol, 1,2-butanediol and 2-methyl-1,3-propanediol are formed from propylene, oxygen and carboxylic acids by way of intermediate steps are disclosed in copending applications A and B discussed above and incorporated herein by reference.

The instant process is carried out in the vapor phase. All of the carboxylic acid monoester is converted directly to tetrahydrofuran and the carboxylic acid, the addition of water being unnecessary. The tetrahydrofuran can be easily isolated by distillation. In contrast, the methods in which water is produced or is otherwise present afford the tetrahydrofuran-water azeotrope, which must be dealt with in another operation to provide anhydrous tetrahydrofuran.

Additionally, if the liquid phase and strong acid catalyst are used, a side reaction occurs, i.e., the following disproportionation:

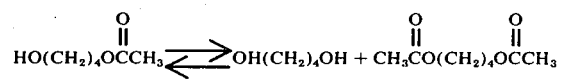

This process competes with tetrahydrofuran formation. The diol formed is easily converted to tetrahydrofuran but the diacetate formed is not. Therefore, a considerable excess of water must be present to hydrolyze the diacetate to the monoacetate so it can eliminate acetic acid and form tetrahydrofuran.

The dehydroacyloxylation mixture can be passed over the catalyst in the liquid phase, vapor phase or liquid-vapor phase. Preferably, it is used in the vapor phase.

For most instances, the reaction is carried out by passing a carboxylic acid monoester of 1,4-butanediol through a heated catalyst bed. Thereafter, the product is distilled to effect isolation of the carboxylic acid and tetrahydrofuran. Well-known techniques of purification of the fractions can be used to obtain the maximum yield of tetrahydrofuran and the carboxylic acid.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

Apparatus — A vertical hot tube reactor (16 mm ID × 70 cm effective length) is constructed from heavy wall glass, with 24/40 male and female joints. Vigreaux points are indented just above the male joint to support catalyst pellets. Thermocouple leads are fastened into three other Vigreaux indentations at points along the length. Three 4 ft. × 1 in. Briskheat glass insulated heating tapes are wound onto the tube, covered with glass wool and glass tape, and connected to separate variable transformers. The tube exit is connected by a gooseneck (also heated) to an efficient condenser and collection vessel. A three necked flask serves as the evaporator, with the reactants added from an addition funnel in a side neck. Nitrogen carrier gas is passed through to provide residence times on the order of 3 to 10 seconds.

EXAMPLE 1

The tube reactor described above is charged with 89 grams of silica-alumina catalyst (87% silica — 13% alumina, 3/16 inch × 3/16 inch pills, Davison Chemical Grade 970) and is maintained at 220°–250° C. while 50.0 grams of a crude oxo product mixture containing, as indicated by quantitative glpc analysis, 31.7 grams of 4-acetoxybutanol, 10.2 grams of 1,4-butanediol diacetate, a very small amount of 1,4-butanediol, and oxo by-products (about 6 grams of acetate derivatives of 2-methyl-1,3-propanediol and 1,2-butanediol) is flash evaporated and passed through over one hour. Quantitative glpc analysis (propionic acid internal standard)

of the effluent shows that no 4-acetoxybutanol remains unconverted, and that 17.3 grams of tetrahydrofuran (100% yield based on the 4-acetoxybutanol initially present) and 17.6 grams of acetic acid have been collected. The 1,4-butanediol diacetate and oxo by-products pass through the tube essentially unchanged.

EXAMPLE 2

A 50.0 gram portion of the same crude oxo product mixture described in Example 1 is passed through the tube containing 85 grams of silica-magnesia catalyst (70% silica — 30% magnesia, 3/16 inch × 3/16 inch pills, Davison Chemical), again at 220°–250° C. and over a one hour period. The results, as indicated by quantitative glpc analysis of the effluent, are substantially the same as in Example 1 — 16.3 grams of tetrahydrofuran (94% yield) and 16.5 grams of acetic acid are collected.

EXAMPLE 3

The tube reactor is charged with 110 grams of alumina catalyst (⅛ inch pellets, Harshaw Al-0104T), which is subsequently subjected to pretreatment at 200° C. with 50% aqueous acetic acid. Then 50.0 grams of a crude oxo product mixture containing, as indicated by quantitative glpc analysis, 24.3 grams of 4-acetoxybutanol, 8.2 grams of 1,4-butanediol diacetate, and oxo by-products (about 5 grams of 3-acetoxy-2-methyl propanol, 6 grams of 2-acetoxybutanol, small amounts of the corresponding diacetates and acetic acid) is flash evaporated and passed through at 200°–220° C over 30 minutes. Quantitative glpc analysis of the effluent shows that no 4-acetoxybutanol remains unconverted and that 12.2 grams of tetrahydrofuran (92% yield based on the 4-acetoxybutanol) and 17.1 grams of acetic acid have been collected. The 1,4-butanediol diacetate passes through the tube unchanged under these conditions.

EXAMPLE 4

The tube reactor is charged with 91 grams of Linde 13X zeolite (⅛ inch pellets) and maintained at 250°–300° C. Four successive 50 gram portions of 4-acetoxybutanol (containing minor amounts of the disproportionation products 1,4-butanediol and 1,4-butanediol diacetate) are passed through over 30 minute periods. The individual effluents are subjected to quantitative glpc analysis; the results are summarized in Table I.

TABLE 1

Product Compositions in the Zeolite-Promoted Production of Tetrahydrofuran from 4-Acetoxybutanol

| Run | Tetrahydrofuran Weight, grams | Yield, % | Acetic Acid Weight, grams | Yield, % |
|---|---|---|---|---|
| 1 | 17.3 | 63 | 3.6 | 16 |
| 2 | 21.4 | 78 | 12.2 | 54 |
| 3 | 21.7 | 80 | 13.2 | 58 |
| 4 | 23.2 | 85 | 14.3 | 63 |

EXAMPLE 5

A miniplant is constructed and operated for the production of tetrahydrofuran from propylene via the disclosed cyclic process. An 8 ft. × 1 in. diameter stainless steel tube is charged with one liter (1000 grams) of catalyst composed of alumina impregnated with palladium (0.3%) and potassium acetate (3%). The reactor temperature is maintained at 180° C. (circulating oil jacket) while a mixture per hour of 2000 grams of propylene, 600 grams of acetic acid, 170 grams of oxygen and 900 grams of water is passed through. The output per hour is a mixture of about 960 grams of allyl acetate and 1050 grams of water, in addition to 18 grams of carbon dioxide and the excess propylene and oxygen, which are recycled. The allyl acetate phase, which contains about 0.1% acetic acid, is separated and used directly in the second stage of the process.

A 2 liter stirred autoclave heated at 125° C. is pressurized with 3000 psi of 2:1 hydrogen/carbon monoxide and charged with a mixture of 400 grams of the allyl acetate, 8.0 grams of cobalt octacarbonyl and 400 ml. of benzene. An exothermic reaction and gas uptake ensue. After 15 minutes at 125°–145° C., the product mixture is pumped from the autoclave, cooled and vented. It is then decobalted by heating at 110° C. for 10 minutes in a closed vessel, the addition of acetic acid being unnecessary because of its presence as a decomposition product. (The cobaltous acetate which forms is filtered off and transformed to cobalt octacarbonyl by subjection to hydrogen/carbon monoxide at elevated temperature and pressure ([160° C., 3000 psi]). The benzene solution is concentrated and the products are flash distilled, affording 474 grams (91% yield) of oxo aldehydes containing minor amounts of the butanediol acetate compounds. A glpc analysis indicates the presence of 4-acetoxybutyraldehyde, 3-acetoxy-2-methylpropionaldehyde and 2-acetoxybutyraldehyde in 7 : 1.5 : 1.5 ratio.

The aldehyde mixture is combined in a stirred autoclave with 50 grams of a 13% cobalt on silica catalyst, subjected to 3000 psi of hydrogen, and heated for 30 minutes at 150° C. Reduction to the diol derivatives is complete, in essentially quantitative yield.

After removal of the hydrogenation catalyst by filtration, the product mixture is examined by glpc and found to contain 4-acetoxybutanol, 3-acetoxy-2-methylpropanol and 2-acetoxybutanol, and small amounts of their respective diacetate and diol disproportionation products.

The acetate mixture is passed directly through an 8 ft. × 1 in. diameter tube containing one liter of the catalyst described in Example 1, at 220° C. and over a 30 minute period (contact time 3 – 10 seconds). Distillation of the effluent affords 184 grams of tetrahydrofuran (64% yield in the conversion from allyl acetate) and 173 grams of acetic acid (72%). The higher boiling components of the effluent include minor amounts of the respective diol diacetates and the by-product monoacetates, from which acetic acid could be derived in a hydrolysis operation. No 4-acetoxybutanol remains unconverted.

The acetic acid produced in the final step is recycled to the propylene oxidation stage for production of allyl acetate.

The process as described is operated semi-continuously to provide tetrahydrofuran at about one pound per hour.

It should, of course, be apparent to those skilled in the art that changes may be made in the particular embodiments of the invention described which are within the full intended scope of the invention as defined by the appended claims.

What is claimed is:

1. A process for preparing tetrahydrofuran which comprises the steps of:

a. reacting propylene, oxygen and a carboxylic acid in the presence of a catalyst comprising a Group VIII noble metal, or its salts, or its oxides or mixtures thereof at a temperature sufficiently high to provide the desired rate of formation of the corresponding allyl carboxylate but below the temperature at which substantial degradation of the allyl carboxylate occurs;

b. converting the allyl carboxylates under hydroformylation-hydrogenation conditions to a mixture comprising the carboxylic acid esters of 1,4-butanediol, 1,2-butanediol and 2-methyl-1,3-propanediol;

c. heating said mixture in the vapor phase in the presence of a dehydroacyloxylation catalyst selected from the group consisting of zeolites, silica, alumina, silica-aluminas, silica-magnesias and acidic clays under substantially anhydrous conditions to produce tetrahydrofuran and the carboxylic acid; and d. isolating the carboxylic acid in a form suitable for recycling to (a).

2. A process for preparing tetrahydrofuran which comprises the steps of:

a. reacting propylene, oxygen and acetic acid in the presence of a catalyst comprising a Group VIII noble metal, or its salts or its oxides or mixtures thereof at a temperature sufficiently high to provide the desired rate of formation of allyl acetate but below the temperature at which substantial degradation of allyl acetate occurs;

b. converting the allyl acetate under hydroformylation-hydrogenation conditions to a mixture comprising the monoacetate esters of 1,4-butanediol, 1,2-butanediol and 2-methyl-1,3-propanediol and their respective diol and diacetate disproportionation products;

c. heating said mixture in the vapor phase in the presence of a dehydroacetoxylation catalyst selected from the group consisting of zeolites, silica, alumina, silica-aluminas, silica-magnesias and acidic clays under substantially anhydrous conditions to produce tetrahydrofuran and acetic acid; and d. isolating the acetic acid in a form suitable for recycling to (a).

* * * * *